US00PP11680P

United States Patent [19]

Lemon

[11] Patent Number: Plant 11,680

[45] Date of Patent: Dec. 12, 2000

[54] VARIETY OF GERANIUM NAMED 'PATRIOT CHERRY ROSE'

[75] Inventor: David G. Lemon, Lompoc, Calif.

[73] Assignee: Oglevee, Ltd., Connellsville, Pa.

[21] Appl. No.: 09/162,746

[22] Filed: Sep. 29, 1998

[51] Int. Cl.[7] ..... A01H 5/00

[52] U.S. Cl. ..... Plt./329

[58] Field of Search ..... Plt./329, 330, 325, Plt./324, 328

[56] References Cited

U.S. PATENT DOCUMENTS

P.P. 5,054 5/1983 Elsner ..... Plt./330

*Primary Examiner*—Howard J. Locker
*Assistant Examiner*—Michelle Kizilkaya
*Attorney, Agent, or Firm*—Webb Ziesenheim Logsdon Orkin & Hanson, P.C.

[57] ABSTRACT

A new and distinct zonal geranium plant with bright cherry pink flowers above medium green foliage. The new variety has a neat, small habit with cutting production, rooting speed and outdoor performance equal to or better than 'Veronica'.

1 Drawing Sheet

BACKGROUND OF THE INVENTION

This invention is directed to a new and distinct variety of geranium identified by the varietal name of 'Patriot Cherry Rose' and Oglevee, Ltd. No. 5003. The new variety was discovered in a selected breeding program by David G. Lemon at Oglevee, Ltd. in Connellsville, Pa. The new variety is a selection from the crossing of the commercial variety 'Americana Rose', U.S. Plant Pat. No. 7,930, and the commercial variety 'Laura', U.S. Plant Pat. No. 7,087. It was first asexually reproduced by cuttings on Jan. 27, 1995 at Connellsville, Pa. and has been found to retains its distinctive characteristics through successive propagations.

The new variety, when grown in a glass greenhouse in Connellsville, Pa. using full light, 60° F. night temperature, 68° F. day temperature and grown in a soilless media with constant fertilizer at 200–250 ppm nitrogen and potassium, has a response time from a rooted cutting to a flowering plant in a 10 inch pot of six weeks.

DESCRIPTION OF THE DRAWING

The accompanying photographic drawing illustrates the new variety, with the color being as nearly true as is possible with color illustrations of this type.

DESCRIPTION OF THE PLANT

The following detailed descriptions set forth the characteristics of the new variety. The data which define these characteristics were collected from asexual reproductions carried out at Oglevee, Ltd., 152 Oglevee Lane, Connellsville, Pa. 15425. The color readings on a plant grown in a 10 inch pot were taken indoors on Jun. 12, 1998 under 200–220 foot candles of cool white fluorescent light. Color references are primarily to the R.H.S. Colour Chart of The Royal Horticultural Society of London.

THE PLANT

Classification:
- *Botanical.*—*Pelargonium×hortorum.*
- *Varietal.*—Florists' zonal geranium named 'Patriot Cherry Rose'.

Form: Medium mound; uniform.
Height: 19.0–20.0 cm from media in a 10 cm pot.
Growth: Free basal branching.

Strength: Needs no artificial support; free flowering; flowers supported on strong stems.
Foliage: Stalked leaf attachment.
Leaves:
- *Size.*—7.5–9.5 cm across.
- *Shape.*—Reniform; cordate base.
- *Margin.*—Crenate.
- *Texture.*—Smooth, pubescent.
- *Color.*—Top: Green Group 137A. Bottom: Yellow-Green Group 147B. Zone: Very faint; Yellow-Green Group 147B.
- *Ribs and veins.*—Venation: Palmate. Color: Yellow-Green Group 146C.

Petioles:
- *Length.*—6.0–7.0 cm long.
- *Color.*—Yellow-Green Group 146B.

Stem:
- *Color.*—Yellow-Green Group 146B.
- *Internode length.*—3.0–4.0 cm.

THE BUD

Overall shape: Elliptical cluster.
Shape of individual bud: Elliptical when bud not showing color and peduncle not fully developed.
Size: 3.0–3.7 cm across when just showing color.

INFLORESCENCE

Blooming habit: Free flowering; continuous; semi-double flowers.
Borne: Umbel, floret on pedicel, pedicel on peduncle.
Closed florets:
- *Bud size.*—0.9–1.2 cm long.

Open florets:
- *Form.*—Flat to slightly cupped.
- *Size of fully open bloom.*—Umbel: 5.0–9.5 cm across. Floret: 2.5–3.0 cm across.
- *Color.*—Top: Overall color Red-Purple Group 57B with white base. Upper three petals are Red-Purple Group 57B at outer edge, blending to Red Group 48C then to Orange-White Group 159D at base. Veining of Red Group 50B present. Bottom: Red Group 52B at edge blending to Red Group 48D. Veining of Red Group 50B shows through. Eye: None observed. Petals: 5–7 in number.

Texture and appearance: Reflective, smooth, velvety; appears from a distance as bright cherry pink flowers above medium green foliage.

Petaloids:

*Quantity.*—2–3.

*Shape.*—Irregular, twisted.

*Color.*—Top: Red-Purple Group 57B. Bottom: Red Group 52B blending to Red Group 48D.

Pedicel:

*Length.*—3.0–4.0 cm.

*Color.*—Yellow-Green Group 146C at base with Red Group 53A at flower base.

Peduncle:

*Length.*—20.0–22.0 cm.

*Color.*—Yellow-Green Group 146B.

Disease resistance: Not known.

Lasting quality: Flowers hold for about 7–14 days.

REPRODUCTIVE ORGANS

Stamens:

*Anthers.*—2–3 mm long.

*Filaments.*—7–9 mm long; white with pink tips.

*Pollen color.*—Golden orange.

Pistils:

*Number.*—1; five parted.

*Length.*—1.0 cm.

*Stigma color.*—Dark magenta.

*Style.*—3 mm long.

*Ovaries.*—Color: Pale green; pubescent; superior; 5 mm long.

Fruit: None observed.

GENERAL CHARACTERISTICS

Cutting production, rooting speed, plant habit and outdoor performance is equal to or better than the current market variety 'Veronica' (U.S. Plant Pat. No. 5,054). The slightly smaller plant habit creates a very profitable finished plant. This variety has been field trialed during the springs and summers of 1995, 1996, 1997 and 1998 and performs well in most weather conditions.

I claim:

1. A new and distinct variety of geranium plant named 'Patriot Cherry Rose' as described and illustrated herein.

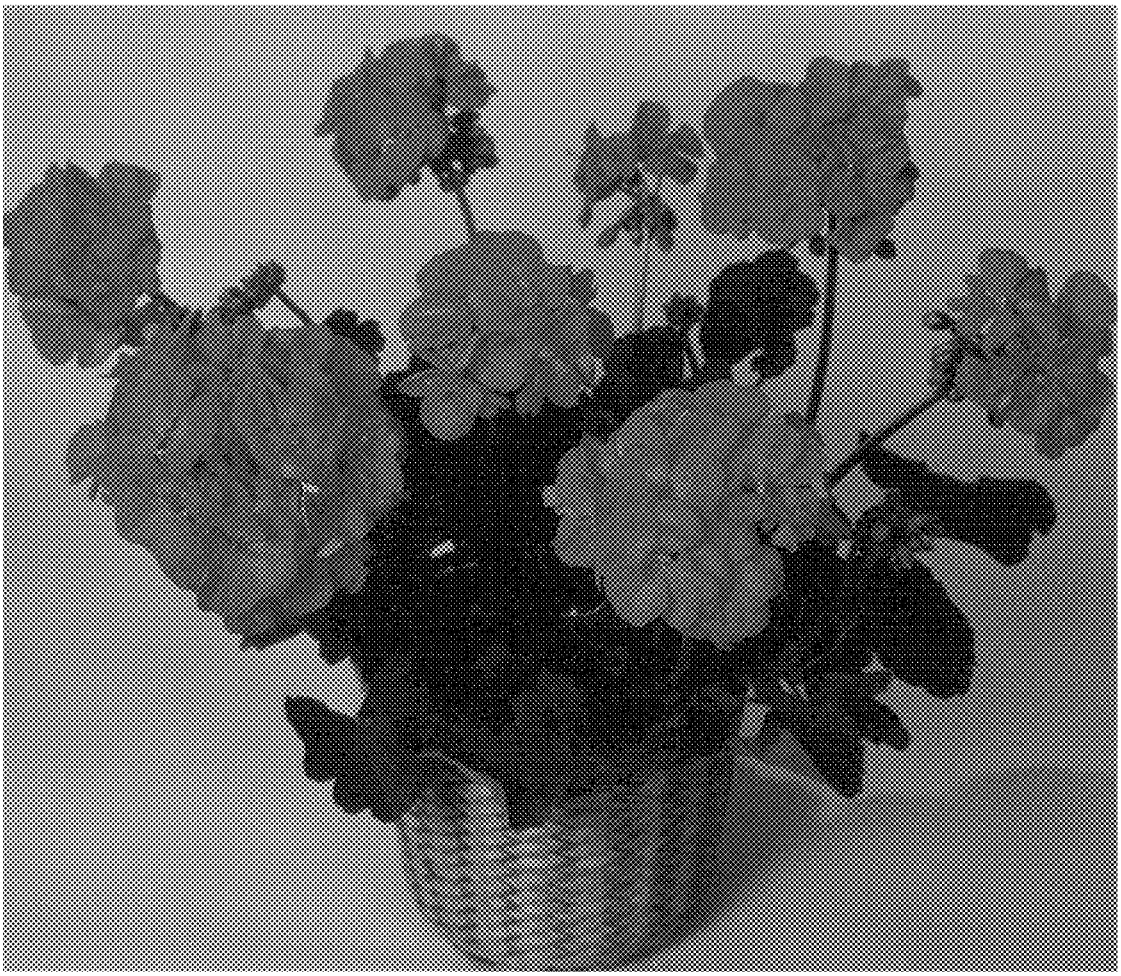

* * * * *